(12) United States Patent
Kim et al.

(10) Patent No.: US 10,131,914 B2
(45) Date of Patent: Nov. 20, 2018

(54) **EXPRESSION CASSETTE INCLUDING AN *RRNA* PROMOTER DERIVED FORM VIBRIO NATRIEGENS FOR ENHANCING THE GROWTH RATE OF *ESCHERICHIA COLI* AND RECOMBINANT *ESCHERICHIA COLI* HAVING THE SAME INTRODUCED THEREINTO**

(71) Applicant: INDUSTRY-ACADEMIC COOPERATION FOUNDATION, YONSEI UNIVERSITY, Seoul (KR)

(72) Inventors: Ji Hyun Kim, Seoul (KR); Ki Tae Kim, Seoul (KR); Soon Kyeong Kwon, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 0 days.

(21) Appl. No.: 15/491,656

(22) Filed: Apr. 19, 2017

(65) Prior Publication Data
US 2017/0298366 A1    Oct. 19, 2017

(30) Foreign Application Priority Data
Apr. 19, 2016    (KR) .......................... 10-2016-0047371

(51) Int. Cl.
*C12N 15/70*    (2006.01)

(52) U.S. Cl.
CPC ........ *C12N 15/70* (2013.01); *C12N 2800/101* (2013.01); *C12N 2830/55* (2013.01)

(58) Field of Classification Search
None
See application file for complete search history.

(56) References Cited

PUBLICATIONS

Aiyar et al. Journal of Bacteriology vol. 184 (2002) pp. 1349-1358.*

* cited by examiner

*Primary Examiner* — James S Ketter
(74) *Attorney, Agent, or Firm* — H.C. Park & Associates, PLC (57) ABSTRACT

The present disclosure relates to an expression cassette including an rrnA promoter derived from *Vibrio natriegens* for enhancing the growth rate of *Escherichia coli* and recombinant *Escherichia coli*, into which the expression cassette is introduced. More particularly, the present disclosure relates to an expression cassette including the *Vibrio natriegens*-derived rrnA promoter for enhancing the growth rate of *Escherichia coli* by introduction thereof into an rrn operon promoter region of *Escherichia coli*.

10 Claims, 5 Drawing Sheets
Specification includes a Sequence Listing.

Recombinant cassette

EXPRESSION CASSETTE INCLUDING AN RRNA PROMOTER DERIVED FORM VIBRIO NATRIEGENS FOR ENHANCING THE GROWTH RATE OF ESCHERICHIA COLI AND RECOMBINANT ESCHERICHIA COLI HAVING THE SAME INTRODUCED THEREINTO

CROSS-REFERENCE TO RELATED APPLICATION

This application claims priority from and the benefit of Korean Patent Application No. 2016-0047371, filed on Apr. 19, 2016, which is hereby incorporated by reference for all purposes as if fully set forth herein.

BACKGROUND

Field

Exemplary embodiments relate to an expression cassette including an rrnA promoter derived from *Vibrio natriegens* for enhancing the growth rate of *Escherichia coli* and a recombinant *Escherichia coli*, into which the expression cassette is introduced, and more particularly, to an expression cassette including an rrnA promoter derived from *Vibrio natriegens* for enhancing the growth rate of *Escherichia coli* by introduction thereof into an rrn operon promoter region of *Escherichia coli*, and a recombinant *Escherichia coli* having the same introduced thereinto.

Discussion of the Background

*Escherichia coli* is the most frequently used microorganism in life sciences and biotechnology due to its various advantages such as the convenience of gene manipulation, and the like. In particular, *Escherichia coli* has been known to be the most suitable for use as a heterologous host for cloning and expression of recombinant genes and proteins to date, and is widely used for the production of medical proteins and enzymes, and the like, and the production of chemicals and medicines using the metabolism mechanism of *Escherichia coli*.

When *Escherichia coli* is cultured at 37° C., it divides once every 20 minutes to 30 minutes under nutrient medium conditions, and once every 40 minutes to 60 minutes under minimal medium conditions. Recently, research into the development of *Escherichia coli* with an enhanced growth rate using genetic engineering and metabolic engineering techniques has been conducted. For example, Hawkins et al. suggested that the growth rate of *Escherichia coli* could be increased by about 7.5% in an Hv-Ca medium by removing a replication initiation site in "Accelerated Growth in the Absence of DNA Replication Origin (2013 Nature)." In addition, Korean Patent Application Publication No. 10-2009-0055989, which is directed to a method of producing hydrogen using *Escherichia coli* transformed with a hox promoter and a hox operon of cyanobacteria, discloses *Escherichia coli* with enhanced hydrogen-producing ability by introducing a promoter of an exogenous species thereinto. However, there is still a need to develop *Escherichia coli* with a significantly increased growth rate at industrial scale.

SUMMARY

Exemplary embodiments of the present disclosure had studied the growth rate of *Escherichia coli* and confirmed that an rrnA promoter derived from *Vibrio natriegens* plays a decisive role in enhancing the growth rate of *Escherichia coli*, and, when the rrnA promoter derived from *Vibrio natriegens* is introduced into an rrn operon promoter region of *Escherichia coli*, the growth rate of *Escherichia coli* could be increased by about 20% or more in a minimal medium, thus completing the invention.

Therefore, the inventors of the present disclosure aim to provide an rrnA promoter derived from *Vibrio natriegens* for enhancing the growth rate of *Escherichia coli*, an expression cassette including the promoter, an expression vector including the expression cassette, *Escherichia coli* transformed with the expression vector, and a method of producing the *Escherichia coli*.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which.

DETAILED DESCRIPTION OF THE ILLUSTRATED EMBODIMENTS

Exemplary embodiments of the present disclosure will be described in detail below with reference to the accompanying drawings. While the present disclosure is shown and described in connection with exemplary embodiments thereof, it will be apparent to those skilled in the art that various modifications can be made without departing from the spirit and scope of the invention.

According to an exemplary embodiment of the present disclosure, there is provided a promoter for enhancing the growth rate of *Escherichia coli*. The promoter is rrnA derived from *Vibrio natriegens*.

The term "promoter" as used herein refers to an upstream nucleic acid sequence of a region encoding amino acids which contains a binding site for RNA polymerase and has the activity of initiating transcription of a promoter downstream gene into mRNA.

The terms "nucleic acid" and "polynucleotide" as used herein interchangeably refer to a polymeric form of nucleotides of any length. These terms include, but are not limited to, single-stranded DNA, double-stranded DNA, genomic DNA, cDNA, or a polypeptide including purine and pyrimidine bases or other naturally, chemically or biochemically modified, non-natural, or derivatized nucleotide bases. Non-limiting examples of suitable polynucleotides include genes, gene fragments, chromosome fragments, ESTs, exons, introns, mRNAs, tRNAs, rrnA, ribozymes, cDNAs, recombinant polynucleotides, branched polynucleotides, plasmids, vectors, any sequence of isolated DNA, any sequence of isolated RNA, nucleic acid probes, and primers. It will be understood that, as a result of degradation of genetic codes, many nucleotide sequences encoding a given protein can be produced.

In the promoter for enhancing the growth rate of *Escherichia coli*, the promoter has a nucleotide sequence of SEQ ID NO: 1.

Figure 1:
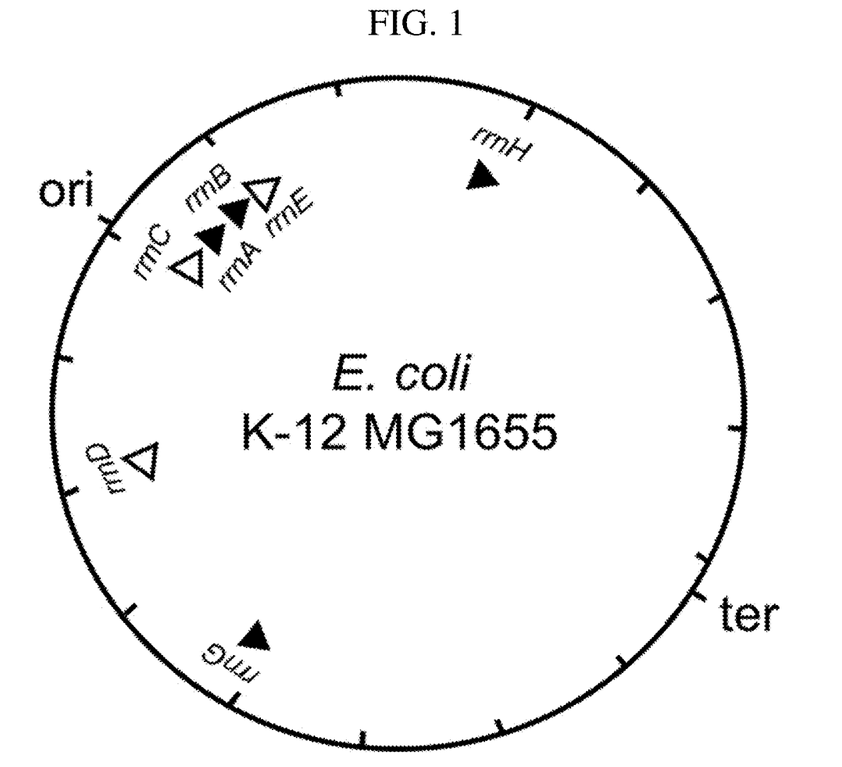
FIG. 1 illustrates a position of an rrn operon on the chromosome in wild-type *Escherichia coli* K-12 MG1655.

In the promoter for enhancing the growth rate of *Escherichia coli*, the promoter is introduced into an rrn operon promoter region of *Escherichia coli*. The rrn operon of *Escherichia coli* may be one or more selected from the group consisting of rrnA, rrnB, rrnC, rrnD, rrnE, rrnG, and rrnH. The position of an rrn operon on the chromosome in wild-type *Escherichia coli* K-12 MG1655 is illustrated in FIG. 1.

In the promoter for enhancing the growth rate of *Escherichia coli*, the promoter is introduced into the rrn operon promoter region of *Escherichia coli*.

According to another exemplary embodiment of the present disclosure, there is provided an expression cassette for enhancing the growth rate of *Escherichia coli*, including the rrnA promoter derived from *Vibrio natriegens*.

The term "expression cassette" as used herein refers to a polynucleotide construct that contains all elements needed for self-expression. Expression cassettes typically include a promoter operably linked to a transgene, a transcription termination signal, a ribosome binding site, and a translation termination signal. The expression cassette may be in the form of a self-replicable expression vector.

The term "operably linked" as used herein indicates that fragments are arranged to be operable during transcription from a promoter to a stop codon through an amino acid-encoding sequence.

The term "selectable marker" as used herein refers to a nucleotide sequence capable of expression in a host cell. Expression of the selectable marker may enable an expressed gene-containing cell to grow in the presence of a corresponding selection agent or in the absence of an essential nutrient.

In the expression cassette for enhancing the growth rate of *Escherichia coli*, the expression cassette may further include one or more selectable markers. The selectable marker may include one or more antibiotic resistance genes selected from the group consisting of chloramphenicol, ampicillin, gentamicin, carbenicillin, streptomycin, kanamycin, geneticin, neomycin, and tetracycline. In addition, the selectable marker may include one or more auxotrophic genes selected from the group consisting of URA3 (uracil auxotroph), LEU2 (leucine auxotroph), TRP1 (tryptophan auxotroph), and HIS3 (histidine auxotroph).

In the expression cassette for enhancing the growth rate of *Escherichia coli*, the promoter has a nucleotide sequence of SEQ ID NO: 1.

In the expression cassette for enhancing the growth rate of *Escherichia coli*, the promoter is introduced into the rrn operon promoter region of *Escherichia coli*. The rrn operon of *Escherichia coli* may be one or more selected from the group consisting of rrnA, rrnB, rrnC, rrnD, rrnE, rrnG, and rrnH.

In the expression cassette for enhancing the growth rate of *Escherichia coli*, the promoter is introduced into the rrnG operon promoter region of *Escherichia coli*.

Figure 2:
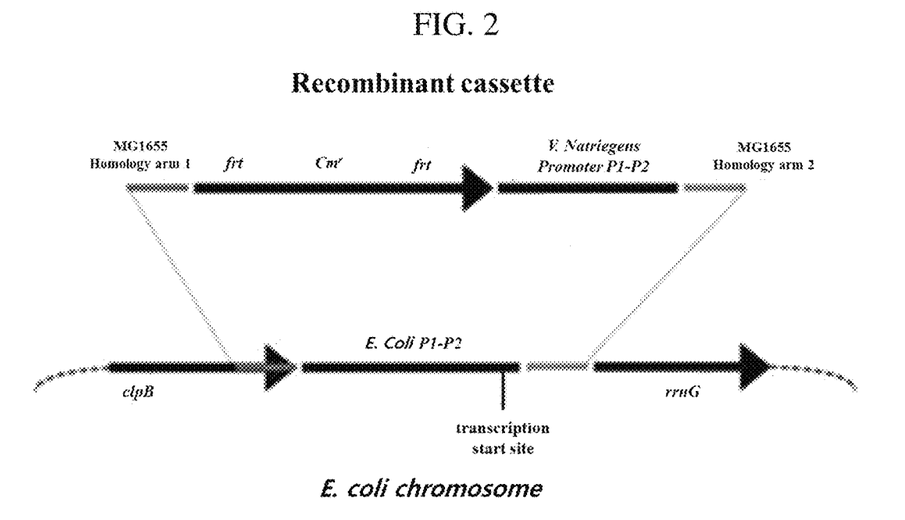
FIG. 2 illustrates a recombinant expression cassette including an rrnA promoter of *Vibrio natriegens* ATCC 14048, to be introduced into an rrn operon promoter of *Escherichia coli*.
Figure 3:
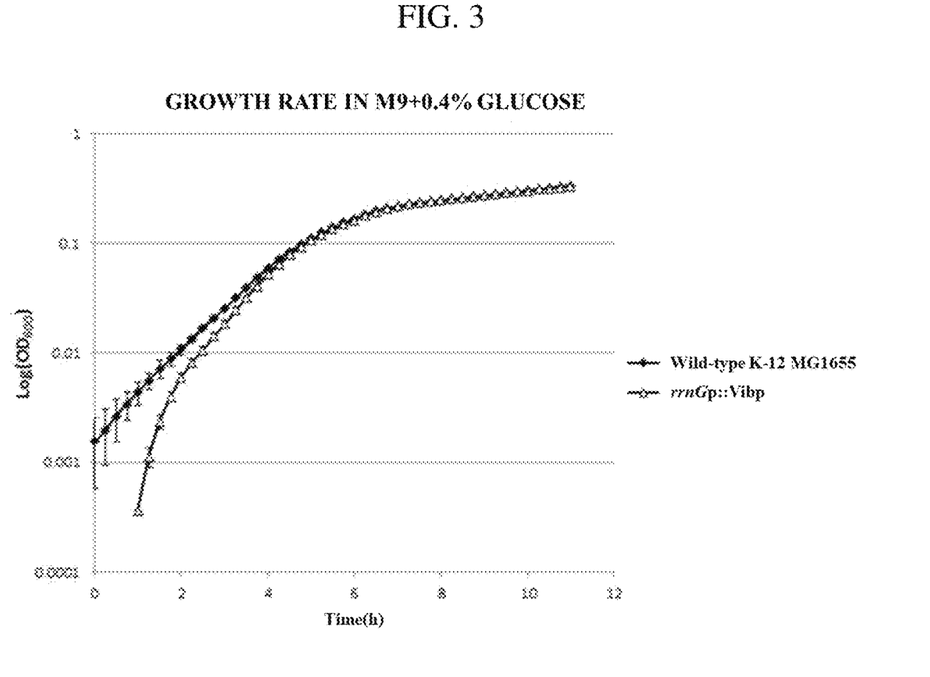
FIG. 3 is a graph showing growth rates of a recombinant *Escherichia coli* (rrnGp::Vibp) according to Example 3 and wild-type *Escherichia coli*.

As an example of the expression cassette for enhancing the growth rate of *Escherichia coli*, a recombinant expression cassette including the rrnA promoter (P1 upstream—248 bp~transcription initiation site +8 bp) of *Vibrio natriegens* ATCC 14048 to be introduced is into the rrnG operon promoter region of *Escherichia coli* (clpB downstream~transcription initiation site +8 bp) is illustrated in FIG. 2.

According to another exemplary embodiment of the present disclosure, there is provided an expression vector for enhancing the growth rate of *Escherichia coli*, including an rrnA promoter derived from *Vibrio natriegens*.

The term "expression vector" as used herein refers to a DNA construct having a polynucleotide base sequence encoding a target protein operably linked to a suitable regulatory sequence so as to be capable of expressing the target protein in a suitable host. The regulatory sequence may include a promoter capable of initiating transcription, any operator sequence for regulating such transcription, a sequence encoding a suitable mRNA ribosome-binding site, and a sequence regulating the termination of transcription and translation. The expression vector may be transformed into a suitable host, and then replicated or function regardless of a host genome, and may be integrated into the genome itself.

In the expression vector for enhancing the growth rate of *Escherichia coli*, the promoter has a nucleotide sequence of SEQ ID NO: 1.

In the expression vector for enhancing the growth rate of *Escherichia coli*, the promoter is introduced into the rrn operon promoter region of *Escherichia coli*. The rrn operon of *Escherichia coli* may be one or more selected from the group consisting of rrnA, rrnB, rrnC, rrnD, rrnE, rrnG, and rrnH.

In the expression vector for enhancing the growth rate of *Escherichia coli*, the promoter is introduced into the rrnG operon promoter region of *Escherichia coli*.

According to another exemplary embodiment of the present disclosure, there is provided a recombinant *Escherichia coli* with an enhanced growth rate into which an expression is cassette or expression vector including an rrnA promoter derived from *Vibrio natriegens* is introduced.

The term "introduction" or "transformation" as used herein refers to the introduction of a gene into a host so that the gene is replicable as an extrachromosomal element or by chromosome integration completion. The transformed gene may be any transformed gene inserted into a chromosome of a microorganism or extrachromosomally positioned so long as it can be expressed in a microorganism. In addition, the gene includes DNA and RNA as a polynucleotide capable of encoding a polypeptide. The gene may be introduced in any form so long as the form allows expression of the gene in a microorganism after introduction. For example, the gene may be introduced into a microorganism in the form of an expression cassette, which is a polynucleotide construct containing all elements needed for self-expression. The expression cassette generally includes a promoter operably linked to the gene, a transcription termination signal, a ribosome-binding site, and a translation termination signal. The expression cassette may be in the form of a self-replicable expression vector. In addition, the gene may be a gene that itself is introduced into a host cell or is introduced in the form of a polynucleotide construct and thus operably linked to a sequence needed for expression in a microorganism.

The term "recombinant" as used herein refers to a polynucleotide or polypeptide that is not naturally present in a host cell.

The term "wild-type" as used herein refers to a host cell that is not genetically modified through recombination.

In the recombinant *Escherichia coli* with an enhanced growth rate, the introduction may be performed by electroporation, a calcium phosphate (CaPO₄) method, a calcium chloride (CaCl₂) method, microinjection, a polyethylene glycol (PEG) method, a diethylaminoethyl (DEAE)-dextran method, a cationic liposome method, or a lithium acetate-DMSO method.

In the recombinant *Escherichia coli* with an enhanced growth rate, the promoter has a nucleotide sequence of SEQ ID NO: 1.

In the recombinant *Escherichia coli* with an enhanced growth rate, the promoter is introduced into the rrn operon promoter region of *Escherichia coli*. The rrn operon of *Escherichia coli* may be one or more selected from the group consisting of rrnA, rrnB, rrnC, rrnD, rrnE, rrnG, and rrnH.

In the recombinant *Escherichia coli* with an enhanced growth rate, the promoter is introduced into the rrnG operon promoter region of *Escherichia coli*.

In the recombinant *Escherichia coli* with an enhanced growth rate, the recombinant *Escherichia coli* has Accession No: KCTC 13006BP.

In the recombinant *Escherichia coli* with an enhanced growth rate, the growth rate of the recombinant *Escherichia coli* is increased by about 10% or more, for example, about 15% or more, for example, about 20% or more compared to that of wild-type *Escherichia coli*.

According to another exemplary embodiment of the present disclosure, there is provided a method of producing a recombinant *Escherichia coli* with an enhanced growth rate. The method includes: (A) producing a recombinant *Escherichia coli* by introducing, into *Escherichia coli*, an expression cassette or expression vector including an rrnA promoter derived from *Vibrio natriegens;* and (B) culturing the recombinant *Escherichia coli*.

In the method of producing a recombinant *Escherichia coli* with an enhanced growth rate, the culturing may be performed using various media known in the art. For example, the medium may include an inorganic component, an organic component, and the like. Non-limiting examples of the inorganic component include phosphorus (P), sulfur (S), calcium (Ca), potassium (K), magnesium (Mg), iron (Fe), manganese (Mn), copper (Cu), zinc (Zn), boron (B), and molybdenum (Mo). Non-limiting examples of the organic component include glucose, sucrose, lactose, rhamnose, arabinose, fructose, glycerol, succinate, fumarate, malate, citrate, acetate, maltose, sorbitol, and starch. In the present exemplary embodiment, an M9 minimal medium was used.

In the method of producing a recombinant *Escherichia coli* with an enhanced growth rate, the promoter has a nucleotide sequence of SEQ ID NO: 1.

In the method of producing a recombinant *Escherichia coli* with an enhanced growth rate, the promoter is introduced into the rrn operon promoter region of *Escherichia coli*. The rrn operon of *Escherichia coli* may be one or more selected from the group consisting of rrnA, rrnB, rrnC, rrnD, rrnE, rrnG, and rrnH.

In the method of producing a recombinant *Escherichia coli* with an enhanced growth rate, the promoter is introduced into the rrnG operon promoter region of *Escherichia coli*.

In the method of producing a recombinant *Escherichia coli* with an enhanced growth rate, the recombinant *Escherichia coli* has Accession No: KCTC 13006BP.

In the method of producing a recombinant *Escherichia coli* with an enhanced growth rate, the growth rate of the recombinant *Escherichia coli* is increased by about 10% or more, for example, about 15% or more, for example, about 20% or more compared to that of wild-type *Escherichia coli*.

According to another exemplary embodiment of the present disclosure, there is provided a method of producing a target protein using the recombinant *Escherichia coli* with an enhanced growth rate. The method includes: (A) producing a recombinant *Escherichia coli* by introducing, into *Escherichia coli*, an expression cassette or expression vector including the rrnA promoter derived from *Vibrio natriegens* and a target protein operably linked to the promoter; (B) culturing the recombinant *Escherichia coli*; and (C) recovering the target protein from the recombinant *Escherichia coli*.

The term "target protein" as used herein refers to a protein or polypeptide produced by a host cell. Generally, a target protein is a commercially important protein. The target protein may be homologous or heterologous with respect to a host. The term "heterologous protein" as used herein refers to a protein or polypeptide that is not naturally present in a host cell. A gene encoding the protein may be a naturally occurring gene, a mutant gene, or a synthetic gene. The term "homologous protein" as used herein refers to an intrinsic or naturally occurring protein or polypeptide in a host cell. The homologous protein may be an intrinsic protein produced by other organisms.

In the method of producing a target protein using the recombinant *Escherichia coli* with an enhanced growth rate, the target protein may be one or more selected from the group consisting of an antigen, an antibody, a cell receptor, an enzyme, a structural protein, serum, and a cell protein.

The rrnA promoter derived from *Vibrio natriegens* may be introduced into the rrn operon promoter region of *Escherichia coli* to enhance the growth rate of *Escherichia coli*, and, as a result, the production of all possible target proteins and secreted metabolites, produced in *Escherichia coli* may be enhanced.

Hereinafter, various examples will be described to help understanding of the invention. However, these examples are provided only for illustrative purposes and are not intended to limit the scope of the invention.

Experimental materials
1. Strains
(1) *Escherichia coli* K-12 MG1655
(2) *Vibrio natriegens* ATCC 14048
2. Primers

| No. | Sequence | SEQ ID NO |
|---|---|---|
| Primer 1 | 5'-AAGTGATTCGCCTGGAAGTTAATGAAG ACCGGATTGTCGCCGTCCAGTAATGTGTAG GCTGGAGCTGCTTC-3' | 2 |
| Primer 2 | 5'-ATACATATGAATATCCTCCTTAGTT-3' | 3 |
| Primer 3 | 5'-ATACATATGGAGCTCGGTCTCCATCTC C-3' | 4 |
| Primer 4 | 5'-AGATTGTCTGATAAATTGTTAAAGAGC AGTGCCGCTTCGCTTTTTCTCAGTCGGAAG AGGCGGCCATTC-3' | 5 |
| Primer 5 | 5'-AAGTGATTCGCCTGGAAGTT-3' | 6 |
| Primer 6 | 5'-AGATTGTCTGATAAATTGTTAAAGA-3' | 7 |
| Primer 7 | 5'-AAGTGATTCGCCTGGAAGTT-3' | 8 |
| Primer 8 | 5'-AGATTGTCTGATAAATTGTTAAAGA-3' | 9 |

EXAMPLE 1

Construction of a Recombinant Expression Cassette

A priming site of vector pKD3 (Datsenko et al., 2009 Proceedings of the National Academy of Sciences U.S.A.), a flippase recognition target (FRT), and a chloramphenicol-resistant gene region were amplified by PCR using primers 1 (SEQ ID NO: 2) and 2 SEQ ID NO: 3) to construct a front part of an expression cassette. Subsequently, in vector pRLG5101 (Aiyar et al., 2002 Journal of Bacteriology) into which the rrnA promoter portion derived from *V. natriegens* was cloned, the promoter region was amplified using primers 3 (SEQ ID NO: 4) and 4 (SEQ ID NO: 5). To select recombinant strains using antibiotics, two amplified products were ligated to each other, and a recognition sequence of an NdeI restriction enzyme was added in front of the rrnA promoter region of *V.* natriegens to thereby link the chloramphenicol-resistant gene region to the rrnA promoter region of *V. natriegens*. The two amplified products were digested with the NdeI restriction enzyme, ligated together by T4 ligase, and then cloned into a pTOP V2 vector (Enzynomics), thereby completing the construction of a recombinant expression cassette.

EXAMPLE 2

Production of Recombinant Expression Cassette-introduced *Escherichia coli*

The recombinant expression cassette constructed according to Example 1 was amplified using primers 5 (SEQ ID NO: 6) and 6 (SEQ ID NO: 7), and a methylated vector was digested with a DpnI restriction enzyme to remove a plasmid that may interfere with an antibiotic resistance selection process. Thereafter, *Escherichia coli* having pKD46 (Datsenko et al., 2009Proceedings of the National Academy of Sciences U.S.A.) needed for linear DNA recombination was cultured in an LB medium supplemented with 100 µg /ml of ampicillin at 30° C., pKD46 was activated by adding 10 mM L-arabinose to the medium when the OD600 nm value reached 0.1, and then further cultured when the OD600 nm value reached 0.5.

A recombinant cassette was inserted into *Escherichia coli* by electroporation, and the recombinant expression cassette-inserted *Escherichia coli* was selected using primers 7 (SEQ ID NO: 8) and 8 (SEQ ID NO: 9) in a LB medium supplemented with 8µg/ml of chloramphenicol through colony PCR. Thereafter, *Escherichia coli* was cultured at 37° C. to remove pKD46, and then inserted into pCP20 (Datsenko et al., 2009 Proceedings of the National Academy of Sciences U.S.A.) by electroporation to remove a chloramphenicol-resistant gene from the chromosome.

*Escherichia coli*, from which an antibiotic-resistant gene was removed, was selected using primers 7 (SEQ ID NO: 8) and 8 (SEQ ID NO: 9) in a solid LB medium through colony PCR, and was cultured at 43° C. to remove pCP20.

EXAMPLE 3

Comparison of the Growth Rates of Recombinant *Escherichia coli* (rrnGp::Vibp) According to the Present Exemplary Embodiment and Wild-type *Escherichia coli*

The recombinant *Escherichia coli* constructed according to Example 2 was cultured in an M9 minimal medium supplemented with 0.4% glucose as a carbon source, and then the growth rate thereof was compared with that of wild-type *Escherichia coli*.

TABLE 2

|  | Wild-type *Escherichia coli* K-12 MG1655 | rrnGp::Vibp |
|---|---|---|
| Specific growth rate (generation/hr) | 0.88 | 1.08 |
| Division time (min) | 47.26 | 38.51 |

As a result, it was confirmed that the growth rate of the recombinant *Escherichia coli* produced according to the present exemplary embodiment (rrnGp::Vibp) was increased by 23.3% compared to that of wild-type *Escherichia coli* K-12 MG1655.

EXAMPLE 4

Figure 4:
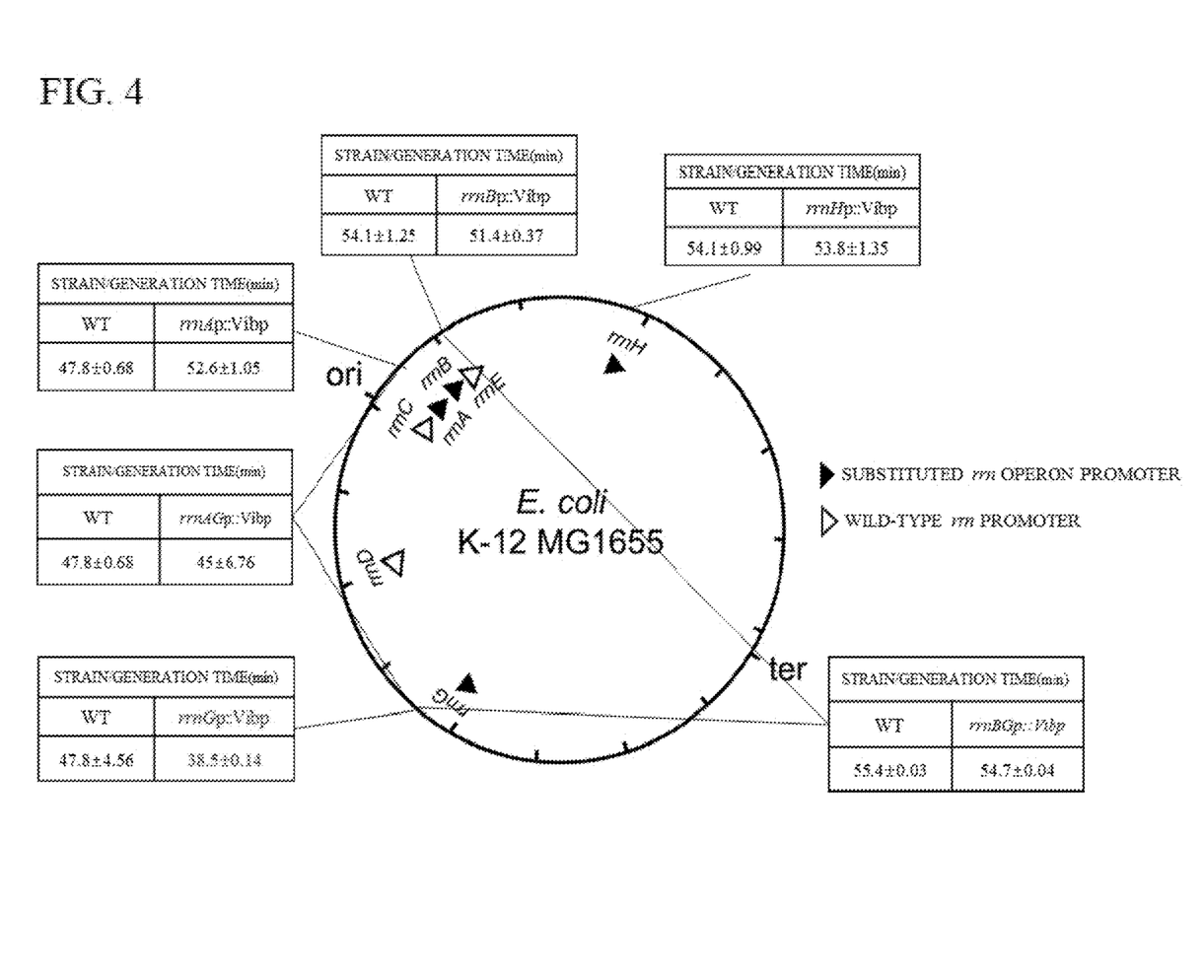
FIGS. 4 and 5 illustrate results of comparing generation times of a recombinant *Escherichia coli* according to rrn operon promoter substitution.
Figure 5:
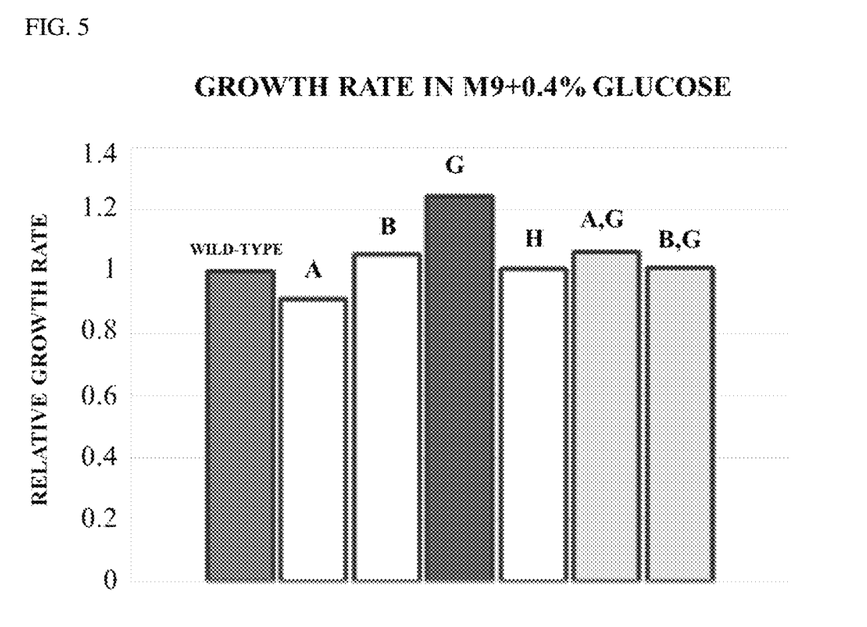

Comparison of the Growth Rates of *Escherichia coli* According to Promoter Substitution FIGS. 4 and 5 illustrate results of comparing generation times of a recombinant *Escherichia coli* according to rrn operon promoter substitution.

Referring to FIGS. 4 and 5, it was confirmed that the recombinant *Escherichia coli* of Example 2 exhibited a significantly higher growth rate than that in a case in which a promoter of SEQ ID NO:1 was introduced into i) the rrnB operon of *Escherichia coli*, or ii) rrnB and rrnG operons by multiple substitution.

In addition, the recombinant *Escherichia coli* of Example 2 exhibited a significantly decreased generation time compared to a case of introduction into the rrnA operon, the rrnH operon, or rrnA and rrnG operons by multiple substitution.

The recombinant *Escherichia coli* exhibited a decreased generation time and a significantly increased growth rate when the promoter of SEQ ID NO: 1 was introduced into the rrnG operon.

The present disclosure has been described with reference to exemplary embodiments. It will be understood by one of ordinary skill in the art to which the present disclosure pertains that the inventive concepts may be embodied in various modified forms without departing from the essential characteristics thereof. Thus, the exemplary embodiments described herein should be considered in an illustrative sense only and not for the purpose of limitation. The scope of the present disclosure is shown not in the above description but in the claims, and all differences within the range equivalent thereto will be interpreted as being incorporated in the present disclosure.

Depository authority: Korea Research Institute of Bioscience and Biotechnology
Accession No: KCTC130006BP
Accession date: Apr. 14, 2016

What is claimed is:

1. An expression cassette comprising a promoter for enhancing a growth rate of *Escherichia coli* by introduction thereof into an rrn operon promoter region of *Escherichia coli*,
wherein the promoter is rrnA derived from *Vibrio natriegens*,
and a selectable marker.

2. The expression cassette according to claim 1, wherein the promoter further comprises a nucleotide sequence of SEQ ID NO: 1.

3. The expression cassette according to claim 1, wherein an rrn operon of *Escherichia coli* is one or more selected from the group consisting of rrnA, rrnB, rrnC, rrnD, rrnE, rrnG, and rrnH.

4. The expression cassette according to claim 1, wherein an rrn operon promoter of *Escherichia coli* is an rrnG operon promoter.

5. The expression cassette according to claim 1, wherein the selectable marker is one or more selected from the group consisting of chloramphenicol, ampicillin, gentamicin, carbenicillin, streptomycin, kanamycin, geneticin, neomycin, and tetracycline.

6. A recombinant *Escherichia coli* with an enhanced growth rate into which the expression cassette according to claim 1 is introduced.

7. The recombinant *Escherichia coli* according to claim 6, wherein the recombinant *Escherichia coli* has Accession No: KCTC 13006BP.

8. The recombinant *Escherichia coli* according to claim 6, wherein the recombinant *Escherichia coli* in which an rrnA promoter derived from *Vibrio natriegens* is introduced into an rrnG operon promoter region.

9. A method of producing a recombinant *Escherichia coli* with an enhanced growth rate, the method comprising:
producing a recombinant *Escherichia coli* by introducing the expression cassette according to claim 1; and
culturing the recombinant *Escherichia coli*.

10. The method according to claim 9, wherein a growth rate of the recombinant *Escherichia coli* is increased by about 10% or more compared to that of wild-type *Escherichia coli*.

* * * * *

UNITED STATES PATENT AND TRADEMARK OFFICE
CERTIFICATE OF CORRECTION

PATENT NO. : 10,131,914 B2  
APPLICATION NO. : 15/491656  
DATED : November 20, 2018  
INVENTOR(S) : Ji Hyun Kim, Ki Tae Kim and Soon Kyeong Kwon

Page 1 of 1

It is certified that error appears in the above-identified patent and that said Letters Patent is hereby corrected as shown below:

On the Title Page

Item (54) and in the Specification, Column 1 Lines 1-7 the Title of Invention should be changed from "EXPRESSION CASSETTE INCLUDING AN RRNA PROMOTER DERIVED FORM VIBRIO NATRIEGENS FOR ENHANCING THE GROWTH RATE OF ESCHERICHIA COLI AND RECOMBINANT ESCHERICHIA COLI HAVING THE SAME INTRODUCED THEREINTO" to --EXPRESSION CASSETTE INCLUDING AN rrnA PROMOTER DERIVED FROM VIBRIO NATRIEGENS FOR ENHANCING THE GROWTH RATE OF ESCHERICHIA COLI AND RECOMBINANT ESCHERICHIA COLI HAVING THE SAME INTRODUCED THEREINTO--.

Signed and Sealed this  
Twenty-second Day of September, 2020

Andrei Iancu  
*Director of the United States Patent and Trademark Office*

SEQUENCE LISTING

<160> NUMBER OF SEQ ID NOS: 9

<210> SEQ ID NO 1
<211> LENGTH: 404
<212> TYPE: DNA
<213> ORGANISM: Vibrio natriegens

<400> SEQUENCE: 1

| | |
|---|---|
| gagctcggtc tccatctcct ataaaagag agctgctgta aagcagctct cttttttact | 60 |
| tatagaagta aaaagcaggg agcaaaaaca ggtatttaag gataactctg tggataacct | 120 |
| gtttgattgt tagggtaaa gttggataaa taaggctttg agtgaaaagt catcgtttag | 180 |
| ccattatttt tgcaaatttt gcaaataac gcttgccaac gtgagcgcga tctctataat | 240 |
| gccacctcgt cgacagggca agcgctcata agggttcaag caaagtcggc aaggtcaaaa | 300 |
| agaaaagcga aatagttaat tgcctttact tttaaaagt aaaataaaaa gcaaaaagtg | 360 |
| tttgacacgg aaaattatct cgctagaatg gccgcctctc ccga | 404 |

<210> SEQ ID NO 2
<211> LENGTH: 71
<212> TYPE: DNA
<213> ORGANISM: Artificial Sequence
<220> FEATURE:
<223> OTHER INFORMATION: Primer 1

<400> SEQUENCE: 2

| | |
|---|---|
| aagtgattcg cctggaagtt aatgaagacc ggattgtcgc cgtccagtaa tgtgtaggct | 60 |
| ggagctgctt c | 71 |

<210> SEQ ID NO 3
<211> LENGTH: 25
<212> TYPE: DNA
<213> ORGANISM: Artificial Sequence
<220> FEATURE:
<223> OTHER INFORMATION: Primer 2

<400> SEQUENCE: 3

| | |
|---|---|
| atacatatga atatcctcct tagtt | 25 |

<210> SEQ ID NO 4
<211> LENGTH: 28
<212> TYPE: DNA
<213> ORGANISM: Artificial Sequence
<220> FEATURE:
<223> OTHER INFORMATION: Primer 3

<400> SEQUENCE: 4

| | |
|---|---|
| atacatatgg agctcggtct ccatctcc | 28 |

<210> SEQ ID NO 5
<211> LENGTH: 69
<212> TYPE: DNA
<213> ORGANISM: Artificial Sequence
<220> FEATURE:
<223> OTHER INFORMATION: Primer 4

<400> SEQUENCE: 5

| | |
|---|---|
| agattgtctg ataaattgtt aaagagcagt gccgcttcgc ttttctcag tcggaagagg | 60 |
| cggccattc | 69 |

<210> SEQ ID NO 6
<211> LENGTH: 20

```
<212> TYPE: DNA
<213> ORGANISM: Artificial Sequence
<220> FEATURE:
<223> OTHER INFORMATION: Primer 5

<400> SEQUENCE: 6
aagtgattcg cctggaagtt                                          20

<210> SEQ ID NO 7
<211> LENGTH: 25
<212> TYPE: DNA
<213> ORGANISM: Artificial Sequence
<220> FEATURE:
<223> OTHER INFORMATION: Primer 6

<400> SEQUENCE: 7
agattgtctg ataaattgtt aaaga                                    25

<210> SEQ ID NO 8
<211> LENGTH: 20
<212> TYPE: DNA
<213> ORGANISM: Artificial Sequence
<220> FEATURE:
<223> OTHER INFORMATION: Primer 7

<400> SEQUENCE: 8
aagtgattcg cctggaagtt                                          20

<210> SEQ ID NO 9
<211> LENGTH: 25
<212> TYPE: DNA
<213> ORGANISM: Artificial Sequence
<220> FEATURE:
<223> OTHER INFORMATION: Primer 8

<400> SEQUENCE: 9
agattgtctg ataaattgtt aaaga                                    25
```